(12) United States Patent
Huynh et al.

(10) Patent No.: US 7,028,387 B1
(45) Date of Patent: Apr. 18, 2006

(54) METHOD OF MAKING A MINIATURIZED POSITIONAL ASSEMBLY

(75) Inventors: Ky Huynh, Tigard, OR (US); Jerome J. Boogaard, Forest Grove, OR (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 374 days.

(21) Appl. No.: 10/397,919

(22) Filed: Mar. 26, 2003

(51) Int. Cl.
*H01F 7/06* (2006.01)
*H01F 5/00* (2006.01)
*B65H 18/28* (2006.01)

(52) U.S. Cl. .................... 29/602.1; 29/605; 29/606; 29/613; 336/200; 242/160.2

(58) Field of Classification Search .............. 29/605, 29/606, 602.1, 613; 336/84, 119, 121, 126, 336/127, 146, 200; 242/160.2, 345.2; 128/899, 128/654, 653.1
See application file for complete search history.

(56) References Cited

U.S. PATENT DOCUMENTS

| | | | |
|---|---|---|---|
| 2,666,906 A | * | 1/1954 | Aust ..................... 336/139 |
| 3,851,287 A | * | 11/1974 | Miller et al. ............... 336/84 R |
| 4,810,917 A | | 3/1989 | Kumar et al. .............. 310/68 R |
| 4,922,199 A | | 5/1990 | Fukui et al. ............ 324/207.17 |
| 5,121,289 A | | 6/1992 | Gagliardi ..................... 361/380 |
| 5,265,322 A | | 11/1993 | Fisher et al. ................... 29/848 |
| 5,325,873 A | * | 7/1994 | Hirschi et al. ............... 128/899 |
| 5,330,128 A | * | 7/1994 | Li et al. ................... 242/345.2 |
| 5,672,967 A | | 9/1997 | Jensen et al. ................ 324/253 |
| 5,786,690 A | | 7/1998 | Kirtley et al. ............... 324/248 |
| 5,908,385 A | | 6/1999 | Chechelski et al. .......... 600/374 |
| 6,025,562 A | | 2/2000 | Shimizu et al. ........... 174/175 F |
| 6,175,756 B1 | | 1/2001 | Ferre et al. .................. 600/424 |
| 6,216,026 B1 | | 4/2001 | Kuhn et al. .................. 600/409 |
| 6,266,551 B1 | * | 7/2001 | Osadchy et al. ............. 600/424 |
| 6,504,366 B1 | | 1/2003 | Bodin et al. ................. 324/247 |

* cited by examiner

*Primary Examiner*—Marc Jimenez
*Assistant Examiner*—Tai Van Nguyen
(74) *Attorney, Agent, or Firm*—Law Office of Timothy E. Sigel; Timothy E. Sigel

(57) ABSTRACT

A method of producing a miniaturized set of inductive coils set mutually orthogonally inside a tube. In the method a positional template made of a sheet of substantially rigid material that defines a set of guide apertures, each of which is in the shape of one of the set of inductive coils. The guide apertures are disposed so that when an inductive coil is fitted into each one of the guide apertures the coils will be substantially orthogonal to one another.

20 Claims, 1 Drawing Sheet

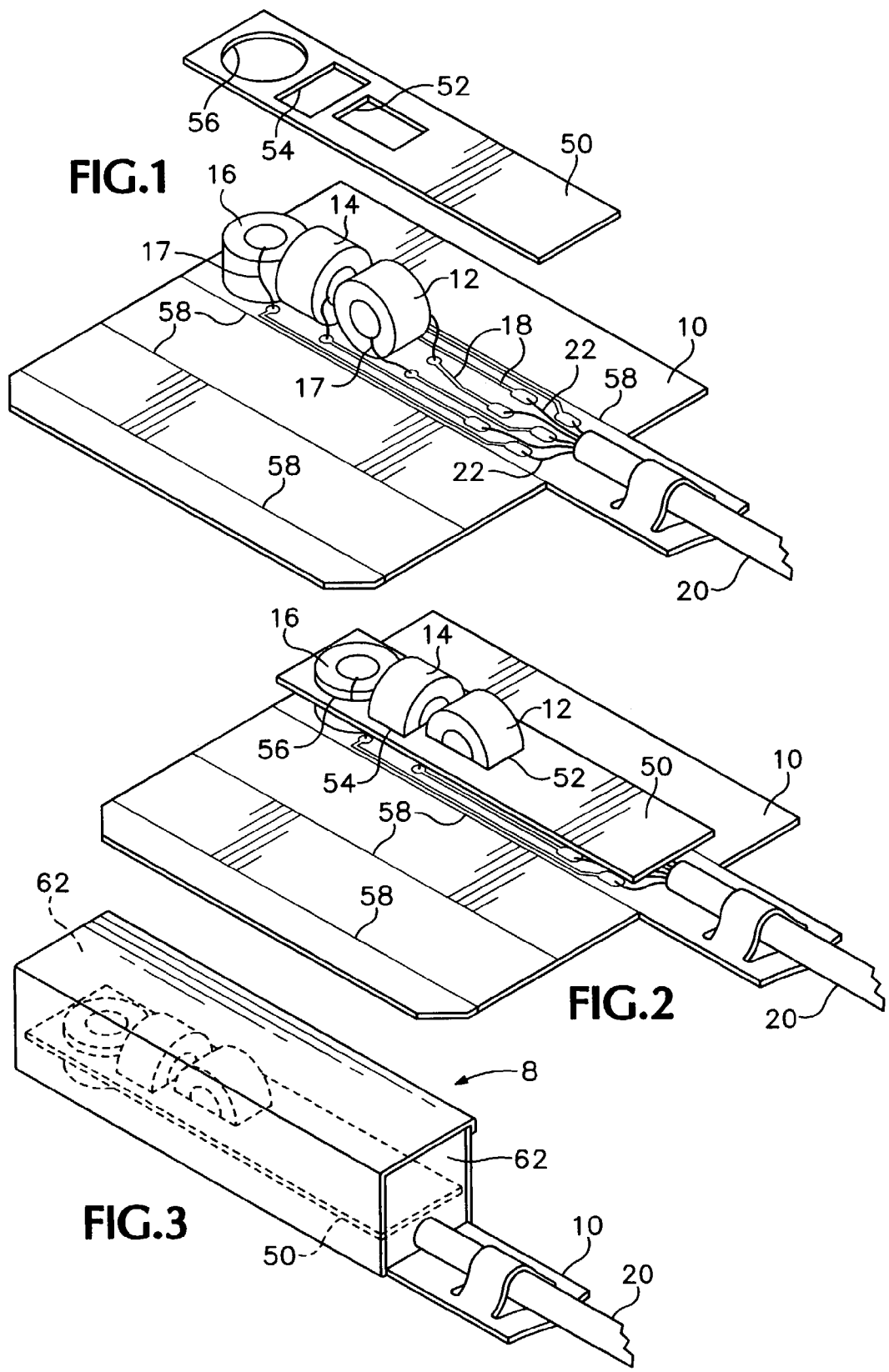

METHOD OF MAKING A MINIATURIZED POSITIONAL ASSEMBLY

BACKGROUND OF THE INVENTION

The ability to accurately determine the position of a device within the body currently yields a considerable benefit for at least one medical procedure. This is the electrophysiological mapping of the heart. Such mapping frequently permits the location and treatment of the neurological disorder that has given rise to a heart arrhythmia. In order to accurately perform this mapping a transceiver head must be introduced into the heart by way (in part) of the femoral artery. The position and orientation of this transceiver head must be accurately monitored.

In order to perform this monitoring a set of orthogonally positioned inductive coils are fixed at the transceiver head and conductively connected through the catheter to the outside of the body, where the current in each of the inductive coils can be read. Cooperating with these coils, powerful magnets are arrayed about the imaging station, so that the current through each coil is dependent on its orientation relative to the magnetic field created.

Heretofore, the manufacture of the unit in which the coils reside has been a challenging and expensive operation. Each coil was soldered to a pair of wires and adjusted so that its position was generally correct. Next the coils and attached wires are gently placed into a polymer tube, which is then filled with epoxy to retain the coils in their generally mutual orthogonal positions and to retain the tube in its protective position.

Performing this method resulted in many problems. First, there was the difficulty in maintaining the mutually orthogonal orientation of the inductive coils during their insertion into the tube and the filling of the tube with epoxy. Also, air pockets would sometimes form as the epoxy was being introduced into the tube.

Another difficulty in the manufacture of a device bearing orthogonally oriented inductive coils is the achievement of true orthogonal orientations. At the fraction of a millimeter scales required to create a device that can be moved through small blood vessels, it is not easy to ensure that each inductive coil is placed within 89.9° and 90.1° of the orientation of the others.

SUMMARY

The present invention is a method of producing a miniaturized set of inductive coils set mutually orthogonally inside a tube. In the method a positional template made of a sheet of substantially rigid material that defines a set of guide apertures, each of which is in the shape of one of the set of inductive coils. The guide apertures are disposed so that when an inductive coil is fitted into each one of the guide apertures the coils will be substantially orthogonal to one another.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1 is a perspective view of a work assembly adapted to be used in the method making a miniaturized positional assembly of the present invention.

FIG. 2 is a perspective view of a work piece, produced from the work assembly of FIG. 1, and constituting a stage in the method of the present invention.

FIG. 3 is a perspective view of a miniaturized positional sensor made from the work piece of FIG. 2.

DETAILED DESCRIPTION OF THE PREFERRED EMBODIMENT

Referring to FIGS. 1–3, in a first preferred embodiment of a method of manufacturing a miniaturized positional assembly 8 (FIG. 3), a piece of flex-circuit 10 is provided that is sized to accommodate a set of inductive coils 12, 14 and 16 when folded into a square tube. The flex circuit has a set of six traces 18, each of which extends from an area adapted to connect to a set of wires 22, to a position adapted to permit the attachment of a terminal 17 of one of the inductive coils 12, 14 and 16. In an alternative preferred embodiment the terminal wires of coils 12, 14 and 16 are extended to attach directly to the ends of wires 22, which are far greater in diameter.

Each of the three coils 12, 14 and 16 may be placed by a robot onto the flex circuit, which preferably has been readied for each with a drop of epoxy to hold the coil in place during further operations. The termini (not shown) of each coil are then soldered to the appropriate flex circuit trace 18. A cable 20 is composed of a set of six wires 22. Each wire 22 is soldered to a circuit trace 18. Although more soldering operations are required than would be necessary if wires 22 were directly soldered to the terminals of the inductive coils 12, 14 and 16, the soldering operations are made far more repeatable and therefore may be automated.

At this point a positional template 50 is lowered into place about said inductive coils 12, 14 and 16. Template 50 defines a first guide aperture 52 adapted to fit closely about inductive coil 12, a second guide aperture 54 adapted to fit closely about aperture inductive coil 14 and a third guide aperture 56 adapted to fit closely about inductive coil 16. When coils 12, 14 and 16 are all fitted into their respective guide apertures 52, 54 and 56, they should be oriented orthogonally to each other in a highly accurate manner.

In an alternative preferred embodiment (not shown) positional template is a flex circuit and inductive coils 12, 14 and 16 are electrically connected to positional template 50.

After the electrical and physical attachment of the inductive coils 12, 14 and 16 to the flex circuit 10, it is curled up in a piecewise manner about a set of laser created score lines 58 to form a tube that is rectangular in cross-section. Epoxy resin may be placed on flex-circuit 10 prior to curling it up into a tube, or epoxy resin could be added at either of a pair of tube openings 62.

The wires used in inductive coils 12, 14 and 16, each has a diameter of from AWG 58 (10 microns) to AWG 50 (25 microns). Each inductive coil 12, 14 and 16 has a diameter of 1 millimeter or smaller. The entire positional assembly 8 is only slightly than the diameter of each individual coil 12, 14 and 16. Accordingly, assembly can also be less than 1 millimeter thick and is approximately 5 millimeters long.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method of producing a miniaturized set of inductive coils set mutually inside a tube, comprising:
   (a) providing a set of inductive coils;
   (b) providing a positional template, including a sheet of substantially rigid material, said sheet defining a set of guide apertures, each guide aperture of the set of guide apertures being in a cross-sectional shape of a respective inductive coil of said set of inductive coils; and
   (c) placing said set of inductive coils into said set of guide apertures, wherein the set of guide apertures cause the set of inductive coils to be substantially orthogonal to one another when the set of inductive coils are placed within the set of guide apertures.

2. The method of claim 1 wherein said inductive coils are first placed onto a platform and are placed into said guide apertures by having said positional template lowered over said inductive coils.

3. The method of claim 2 wherein said platform is a flex circuit, to which said inductive coils are electrically connected.

4. The method of claim 2 wherein said platform is curled about said inductive coils to form a protective tube.

5. The method of claim 4, wherein said platform is scored and is curled in a piecewise fashion about said inductive coils to form a protective tube that is rectangular in cross-section.

6. A method of producing a miniaturized positional sensor for identifying a position within a patient, the method comprising:
   providing a flex circuit including a plurality of electrical traces;
   coupling a set of inductive coils to the plurality of electrical traces, wherein each inductive coil of the set of inductive coils has a three-dimensional shape that is substantially cylindrical; and
   positioning the set of inductive coils within a positional template, wherein (i) the positional template includes a plurality of guide apertures with each guide aperture of the plurality of guide apertures having a cross-sectional shape of a respective inductive coil of the set of inductive coils and (ii) the set of guide apertures cause the set of inductive coils to be substantially orthogonal to one another when the set of inductive coils are placed within the positional template.

7. The method of claim 6 wherein each inductive coil of the set of inductive coils has a diameter less than or equal to one millimeter.

8. The method of claim 6 wherein the flex circuit is less than or equal to five millimeters in length.

9. The method of claim 6 wherein the coupling comprises:
   soldering wire connections between the plurality of electrical traces and the set of inductive coils.

10. The method of claim 6 further comprising:
    folding the flex circuit to form an enclosure that substantially surrounds the set of inductive coils.

11. The method of claim 10 wherein the enclosure is curled around the set of inductive coils.

12. The method of claim 10 wherein the enclosure is rectangular.

13. The method of claim of 6 further comprising:
    providing epoxy material to affix the set of inductive coils to the flex circuit.

14. The method of claim 6 further comprising:
    coupling a cable to the plurality of electrical traces of the flex circuit.

15. A method of producing a miniaturized positional sensor for identifying a position within a patient, the method comprising:
    providing a flex circuit including a plurality of electrical traces and a plurality of guide apertures;
    positioning a set of inductive coils within the plurality of guide apertures, wherein (i) each inductive coil of the set of inductive coils has a three-dimensional shape; (ii) each guide aperture of the plurality of guide apertures has a cross-sectional shape of a respective inductive coil of the set of inductive coils; and (iii) the plurality of guide apertures cause the set of inductive coils to be substantially orthogonal to one another when the set of inductive coils are placed within the plurality of guide apertures;
    electrically coupling the set of inductive coils to the plurality of electrical traces; and
    enclosing the set of inductive coils within an enclosure.

16. The method of claim 15 wherein the three-dimensional shape is cylindrical.

17. The method of claim 15 wherein the electrical coupling includes soldering wire connections between the plurality of electrical traces and the set of inductive coils.

18. The method of claim 15 further comprising:
    coupling a cable to the plurality of electrical traces of the flex circuit.

19. The method of claim 15 wherein each inductive coil of the set of inductive coils has a diameter of less than or equal to one millimeter.

20. The method of claim 15 wherein the flex circuit has a length of less than or equal to five millimeters.

* * * * *